(12) United States Patent
Boffeli et al.

(10) Patent No.: US 11,980,372 B2
(45) Date of Patent: May 14, 2024

(54) OSTEOTOMY FIXATION DEVICE AND RELATED SYSTEMS AND METHODS

(71) Applicant: TRILLIANT SURGICAL, LLC, Houston, TX (US)

(72) Inventors: Troy J. Boffeli, Woodbury, MN (US); Shannon M. Rush, San Jose, CA (US); Graham Hamilton, Concord, CA (US); Michael Lee, Johnston, IA (US); Jordan Grossman, Akron, OH (US); Mark Hardy, Lakewood, OH (US); David Kawalik, Chandler, AZ (US)

(73) Assignee: Trilliant Surgical, LLC, Houston, TX (US)

( * ) Notice: Subject to any disclaimer, the term of this patent is extended or adjusted under 35 U.S.C. 154(b) by 368 days.

(21) Appl. No.: 17/242,991

(22) Filed: Apr. 28, 2021

(65) Prior Publication Data

US 2021/0330335 A1 Oct. 28, 2021

Related U.S. Application Data

(60) Provisional application No. 63/016,487, filed on Apr. 28, 2020.

(51) Int. Cl.
*A61B 17/15* (2006.01)
*A61B 17/56* (2006.01)

(52) U.S. Cl.
CPC ...... *A61B 17/151* (2013.01); *A61B 2017/565* (2013.01)

(58) Field of Classification Search
CPC ....... A61B 17/15; A61B 17/151; A61B 17/66; A61B 17/17; A61B 17/1775; A61B 17/80; A61B 17/8061; A61B 17/84; A61B 17/848
See application file for complete search history.

(56) References Cited

U.S. PATENT DOCUMENTS

| | | | |
|---|---|---|---|
| 8,282,645 B2 | 10/2012 | Lawrence et al. |
| 8,858,602 B2 | 10/2014 | Weiner et al. |
| 9,017,334 B2 | 4/2015 | Carroll et al. |
| 9,089,342 B2 | 7/2015 | Carroll et al. |
| 9,101,421 B2 | 8/2015 | Blacklidge |

(Continued)

FOREIGN PATENT DOCUMENTS

| | | |
|---|---|---|
| WO | 2020041841 A1 | 3/2020 |
| WO | 2021222415 A1 | 11/2021 |

OTHER PUBLICATIONS

International Preliminary Report on Patentability Received for PCT Application Serial No. PCT/US2021/029658 dated Nov. 10, 2022, pages.

(Continued)

*Primary Examiner* — Christopher J Beccia
(74) *Attorney, Agent, or Firm* — Veros Legal Solutions, LLP

(57) ABSTRACT

An all-in-one osteotomy fixation device, along with various related components, systems, and methods. The various embodiments include a device body, a bone attachment structure, a removable slot body, and a movable cutting guide moveably attached to the body via a guide coupling structure. The various methods include using any single device embodiment herein to perform all of the steps of the osteotomy procedure.

11 Claims, 8 Drawing Sheets

(56) References Cited

U.S. PATENT DOCUMENTS

| | | |
|---|---|---|
| 9,433,452 B2 | 9/2016 | Weiner et al. |
| 9,566,096 B2 | 2/2017 | Blacklidge |
| 9,687,250 B2 | 6/2017 | Dayton et al. |
| 10,064,665 B2 | 9/2018 | Blacklidge |
| 10,512,470 B1 | 12/2019 | Bays et al. |
| 10,524,808 B1 | 1/2020 | Hissong et al. |
| 10,610,241 B2 | 4/2020 | Wagner et al. |
| 10,653,465 B2 | 5/2020 | Blacklidge |
| 10,729,453 B2 | 8/2020 | Woodard et al. |
| 10,786,291 B2 | 9/2020 | Weiner et al. |
| 2002/0164905 A1 | 11/2002 | Bryant |
| 2013/0060253 A1* | 3/2013 | Couture ................. A61B 90/50 |
| | | 606/88 |
| 2016/0235414 A1 | 8/2016 | Hatch et al. |
| 2016/0367298 A1 | 12/2016 | Weiner et al. |
| 2017/0014143 A1* | 1/2017 | Dayton .............. A61B 17/8061 |
| 2018/0228498 A1 | 8/2018 | Dacosta et al. |
| 2018/0250024 A1 | 9/2018 | Woodard et al. |
| 2020/0060690 A1* | 2/2020 | Woodard ........... A61B 17/8866 |
| 2020/0170655 A1 | 6/2020 | Zakhary et al. |
| 2020/0229828 A1 | 7/2020 | Wagner et al. |
| 2020/0237417 A1 | 7/2020 | Blacklidge |
| 2020/0330109 A1 | 10/2020 | Woodard et al. |
| 2021/0259749 A1* | 8/2021 | Lam ....................... A61B 17/84 |
| 2021/0330335 A1 | 10/2021 | Boffeli et al. |

OTHER PUBLICATIONS

International Search Report and Written Opinion, dated Nov. 4, 2021 in PCT/US2021/029658.

\* cited by examiner

CROSS-REFERENCE TO RELATED APPLICATION(S)

This application claims the benefit under 35 U.S.C. § 119(e) to U.S. Provisional Application 63/016,487, filed Apr. 28, 2020 and entitled "Osteotomy Fixation Device and Related Systems and Methods," which is hereby incorporated herein by reference in its entirety.

FIELD

The various embodiments herein relate to bone deformity treatment methods and devices, including, for example, osteotomy fixation devices.

BACKGROUND

Various known osteotomy procedures are used to treat bone deformities. For example, distal metatarsal osteotomy ("DMO") is the most common procedure used in hallux valgus (bunion) surgery. Little has changed in the last 20 to 30 years with respect to the technologies and methods utilized for DMO procedures. Surgeons typically choose from a variety of known osteotomy configurations, including the standard V cut Austin, long dorsal arm Austin, long plantar arm Austin, and a flat cut if frontal plane correction is desired. Fixation after the procedure typically involves either (1) a temporary K-wire placed percutaneously thru the skin, or, more recently, (2) the use of compression screws, which avoids external pins, provides compression, and provides more stable fixation.

One disadvantage with the known DMO procedures generally is that the distal fragment (metatarsal head) is small and largely covered with cartilage and therefore has limited areas for screw purchase. The main weakness of screw fixation is that the bone in the metatarsal head is frequently soft and cystic due to longstanding deformity, chronic inflammation, DJD, RA, gout, age, osteoporosis, or other such conditions. Thus, screw purchase can be compromised and/or screws are prone to loosen over time, such that intraop or postop screw failure is common. In addition, the screws commonly must be removed with a second surgery due to prominence and pain. A further disadvantage is that screws sometimes limit the amount of bone that can be removed dorsally or medially due to fear of destabilizing the osteotomy. In addition, a further complication is early loss of screw purchase with secondary displacement of the capital fragment dorsally, plantarly, or laterally into the intermetatarsal space. This complication is hard to rectify due to limited fixation options and causes long term problems like hallux varus (over-correction of deformity if left untreated).

Other challenges with known DMO procedures and devices involve the difficulty with making a consistent osteotomy and manually transposing the head in the lateral direction. Surgeons also want the option of a flat cut osteotomy which allows frontal plane correction, but this configuration is difficult to fixate unless a fixation plate is used. One disadvantage of known fixation plates for DMO #3279169 fixation is that they are applied medially on the metatarsal head. The plates tend to be bulky on the medial side and can cause medial shoe irritation.

Another disadvantage of known DMO procedures is that they generally don't include any type of jig or guiding structure for aiding the surgeon with osteotomy, transposition, or fixation. As a result, many known DMO procedures can be challenging procedures that require multiple devices, creating the need for more than one person to perform the procedures in certain instances and increased risk for mistakes and lack of uniformity and precision with respect to the cutting and positioning of the target bones.

There is a need in the art for an improved osteotomy fixation devices and related systems and methods.

BRIEF SUMMARY

Discussed herein are various embodiments of an osteotomy fixation system, including a system having a jig and a fixation plate, and related devices and methods.

In Example 1, an osteotomy device comprises a device body comprising a bone attachment structure and a guide coupling structure comprising a rod rotatably associated with the coupling structure. In addition, the device further comprises a movable cutting guide threadably coupled to the rod and a slot body removably attachable to the device body, wherein the slot body comprises a transverse slot defined within the slot body.

Example 2 relates to the osteotomy device according to Example 1, wherein the movable cutting guide comprises a transposition mechanism threadably coupled thereto, wherein the transposition mechanism comprises a rotatable elongate body and a distal plate attached to a distal end of the rotatable elongate body.

Example 3 relates to the osteotomy device according to Example 2, wherein the distal plate is a rotatable circular plate.

Example 4 relates to the osteotomy device according to Example 2, wherein the rotatable elongate body is a threaded rotatable elongate body disposed through a threaded guide lumen defined in the movable cutting guide.

Example 5 relates to the osteotomy device according to Example 1, wherein the movable cutting guide comprises a proximal guide edge.

Example 6 relates to the osteotomy device according to Example 1, wherein the moveable cutting guide comprises an attachment body, wherein the attachment body comprises a threaded attachment lumen.

Example 7 relates to the osteotomy device according to Example 5, wherein the rod comprises a threaded rod disposed within and threadably coupled with the threaded attachment lumen.

Example 8 relates to the osteotomy device according to Example 1, wherein the movable cutting guide comprises a first opening and a second opening. The first opening is defined in the movable cutting guide, the first opening comprising a threaded opening configured to receive a transposition mechanism threadably coupled therein, wherein the transposition mechanism comprises a threaded rotatable elongate body and a distal plate attached to a distal end of the rotatable elongate body. The second opening is defined in the movable cutting guide, the second opening configured to receive an attachment pin.

In Example 9, an osteotomy system comprises a fixation and guide device attachable to a target bone and a fixation plate attachable to a portion of the target bone after removal of the slot body. The fixation and guide device comprises a device body comprising a bone attachment structure and a guide coupling structure comprising a rod rotatably associated with the coupling structure. The device further comprises a movable cutting guide threadably coupled to the rod and a slot body removably attachable to the device body, wherein the slot body comprises a transverse slot defined within the slot body.

Example 10 relates to the osteotomy system according to Example 9, wherein the movable cutting guide comprises a transposition mechanism threadably coupled thereto, wherein the transposition mechanism comprises a rotatable elongate body and a distal plate attached to a distal end of the rotatable elongate body.

Example 11 relates to the osteotomy system according to Example 10, wherein the distal plate is a rotatable circular plate.

Example 12 relates to the osteotomy system according to Example 10, wherein the rotatable elongate body is a threaded rotatable elongate body disposed through a threaded guide lumen defined in the movable cutting guide.

Example 13 relates to the osteotomy system according to Example 9, wherein the movable cutting guide comprises a proximal guide edge.

Example 14 relates to the osteotomy system according to Example 9, wherein the moveable cutting guide comprises an attachment body, wherein the attachment body comprises a threaded attachment lumen.

Example 15 relates to the osteotomy system according to Example 14, wherein the rod comprises a threaded rod disposed within and threadably coupled with the threaded attachment lumen.

Example 16 relates to the osteotomy system according to Example 9, wherein the movable cutting guide comprises a first opening and a second opening. The first opening is defined in the movable cutting guide, the first opening comprising a threaded opening configured to receive a transposition mechanism threadably coupled therein, wherein the transposition mechanism comprises a threaded rotatable elongate body and a distal plate attached to a distal end of the rotatable elongate body. The second opening is defined in the movable cutting guide, the second opening configured to receive an attachment pin.

Example 17 relates to the osteotomy system according to Example 9, wherein the bone attachment structure comprises at least two fixation screw openings defined therein, wherein the bone attachment structure has a curved face configured to be contactable with the target bone.

Example 18 relates to the osteotomy system according to Example 9, wherein the moveable cutting guide is moveable along a path substantially parallel with a length of the target bone.

Example 19 relates to the osteotomy system according to Example 9, wherein the moveable cutting guide comprises a transposition rod threadably coupled to the moveable guide, wherein the transposition rod comprises a distal plate attached to a distal end of the transposition rod, wherein rotation of the transposition rod causes transverse movement of the transposition rod in relation to a longitudinal axis of the target bone.

In Example 20, a method of performing an osteotomy comprises positioning an osteotomy device adjacent to a target bone, the osteotomy device comprising a device body comprising a bone attachment structure and a guide coupling structure comprising a rod rotatably associated with the coupling structure. The device further comprises a movable cutting guide threadably coupled to the rod and a slot body removably attachable to the device body, wherein the slot body comprises a transverse slot defined within the slot body. The method further comprises inserting a first anchoring pin through the transverse slot and into the target bone, inserting a second anchoring pin through an opening defined in the bone attachment structure and into the target bone, making a desired cut in the target bone with a saw blade positioned against the movable cutting guide, resulting in a base bone and a cut bone, inserting a transposition mechanism through the movable cutting guide and into the cut bone, urging the cut bone distally from the base bone by rotating the rod associated with the coupling structure, urging the cut bone laterally by actuating the transposition mechanism, urging the cut bone proximally into contact with the base bone by rotating the rod associated with the coupling structure, removing the slot body from the device body, and attaching a fixation plate to the cut bone and the base bone.

While multiple embodiments are disclosed, still other will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

DETAILED DESCRIPTION

Figure 1A:
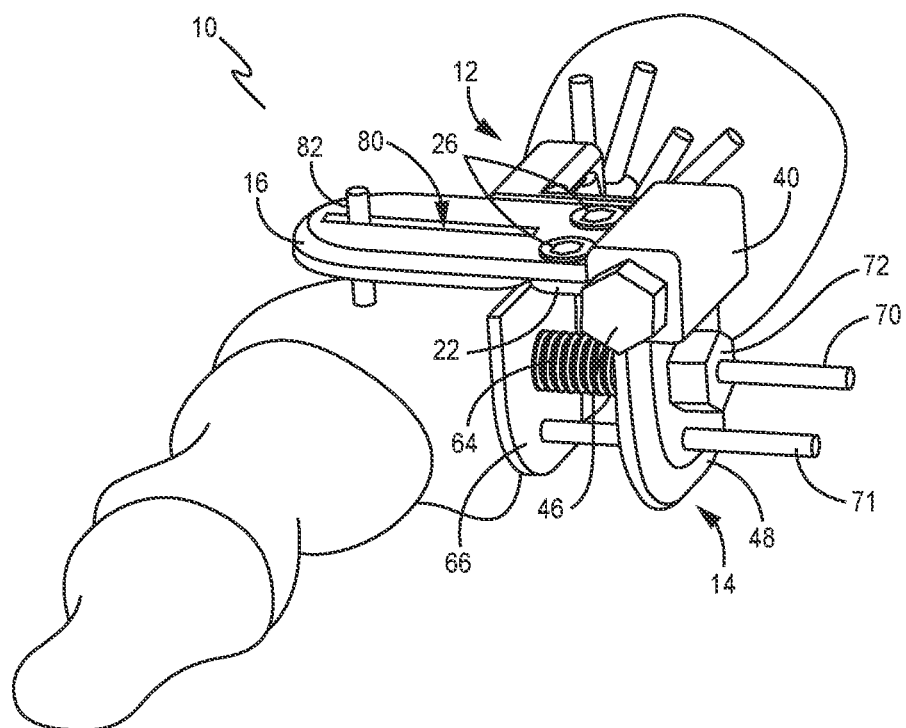
FIG. 1A is a perspective front view of a guide device, according to one embodiment.

The various embodiments disclosed or contemplated herein relate to improved systems, devices, and methods, and various components thereof, relating to osteotomy fixation. Such systems, devices, and methods can be utilized or performed on any bones, including, for example, any bones of a patient's extremities, such as two or more bones of a patient's hand and/or two or more bones of a patient's foot. Certain exemplary implementations herein are utilized on metatarsals, but it is understood that the implementations disclosed or contemplated herein can be utilized on any human bones requiring such treatment. More specifically, the implementations relate to a osteotomy fixation device and related systems and methods designed to allow for an attached jig and a unique fixation plate. Further, certain embodiments relate specifically to a osteotomy fixation device for use in treating hallux valgus. Various implementations relate to an all-in-one, adjustable device that can be affixed to the target bone to provide an osteotomy guide along with the capability to move the target bone both axially (to distract or compress the bone) and laterally (to transpose the bone).

FIGS. 1A-1D depict one embodiment of a guide device or "jig" 10, which is one component (along with a fixation plate 100, according to certain implementations as discussed in additional detail below) of the osteotomy procedure system, according to one implementation. The jig 10 has a body (also referred to as a "jig body" or "device body") 12, a movable cutting guide 14 movably coupled to the body 12 at a guide coupling structure 40, and a removable slot body (also referred to herein as a "wing") 16 removably attached to the body 12.

The device body 12 has a bone attachment structure (also referred to as a "dorsal fixation section") 13 at or near a proximal end of the body 12, along with the guide coupling structure 40 discussed above at or near the distal end. As best shown in FIGS. 1B and 1F, the bone attachment structure 13 in this specific embodiment is curved or otherwise shaped to optimize its contact with and attachment to the bone to which it is attached. Further, the bone attachment structure 13 in this exemplary implementation has four anchor openings 18 defined therein, wherein each of the anchor openings 18 is configured to receive an anchor pin 20 as shown such that the anchor pins 20 are embedded into or "anchored" in the dorsal portion of the target bone. Alternatively, the bone attachment structure 13 can be shaped in any fashion that enhances contact with the target bone and can have at least one anchor opening and a corresponding at least one anchor pin. In one embodiment, the anchor pins 20 (and all other "anchor pins" used in the various system embodiments as disclosed or contemplated herein) are known K wires. Alternatively, it is understood that the anchor pins (including 20) described herein can be any known elongate anchoring or fixation mechanisms or devices that can be used with bone fixation devices.

In one embodiment, the jig body 12 is made of metal or plastic of an appropriate rigidity. More specifically, some exemplary materials that can make up the jig body 12 include any known medical grade stainless steel alloys, titanium alloys, thermoplastics, and/or thermosets/resins. Alternatively, the body 12 can be made of any known material of appropriate rigidity that can be used in such bone treatment devices. Further, it is understood that any of the other structures and/or components of the device 10 can also be made up of the same or similar materials.

Figure 1B:
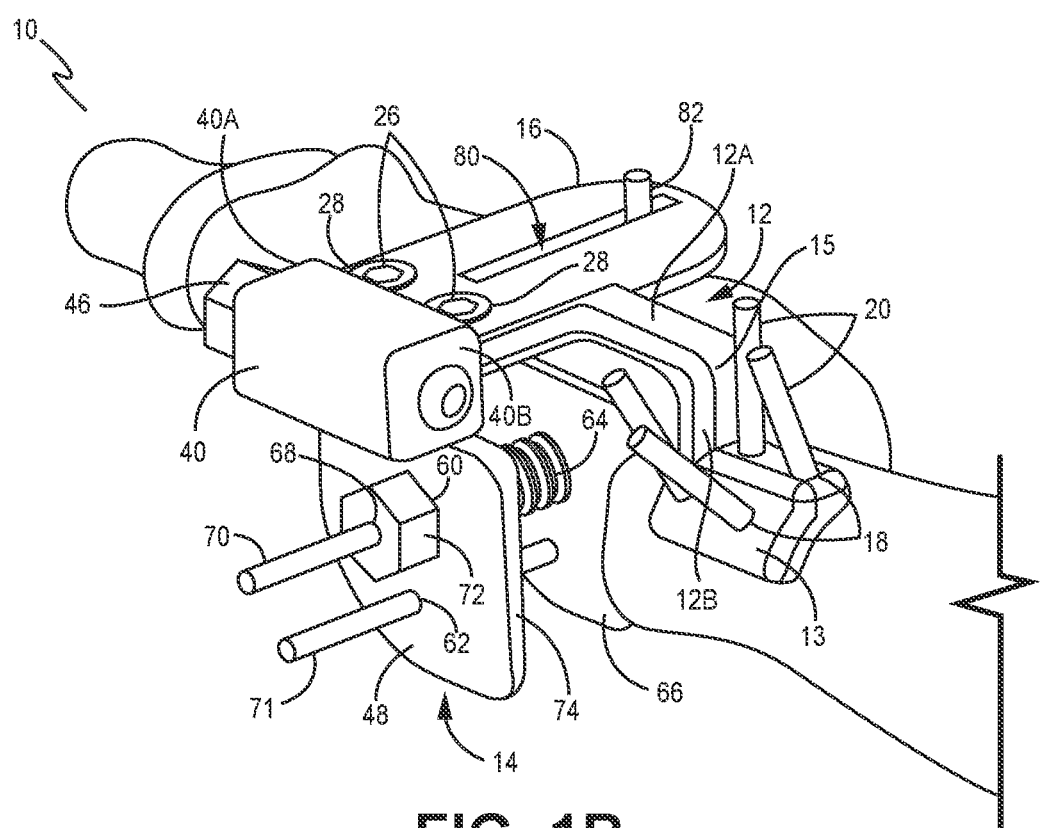
FIG. 1B is a perspective rear view of the guide device of FIG. 1A, according to one embodiment.
Figure 1C:
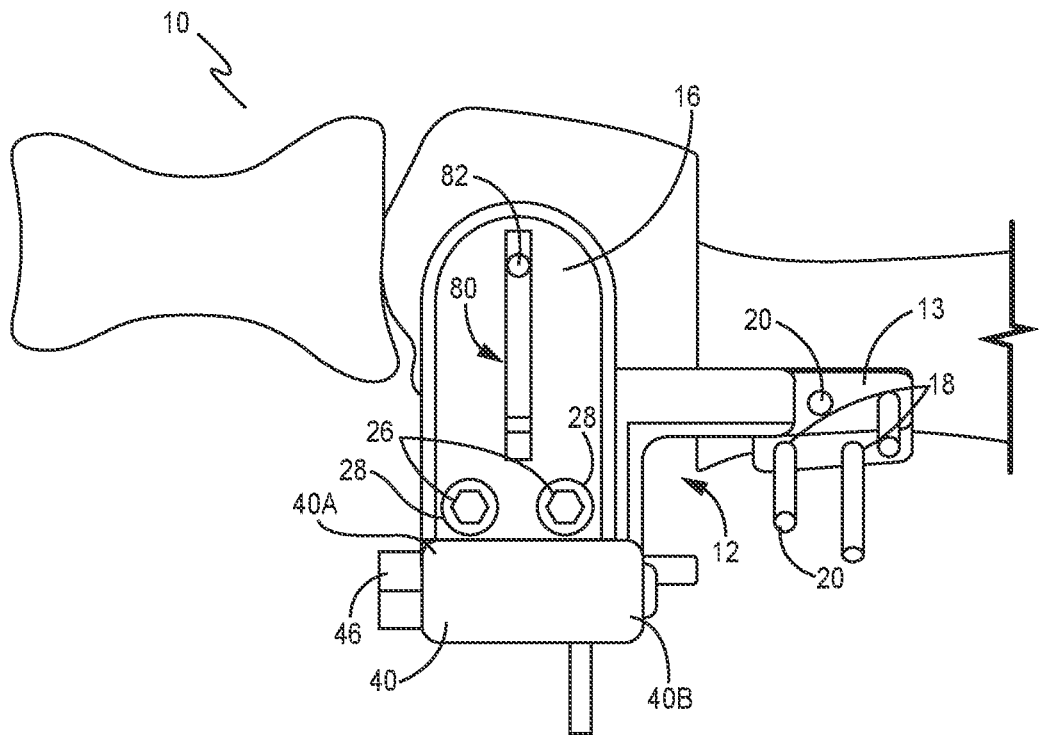
FIG. 1C is a top view of the guide device of FIG. 1A, according to one embodiment.
Figure 2:
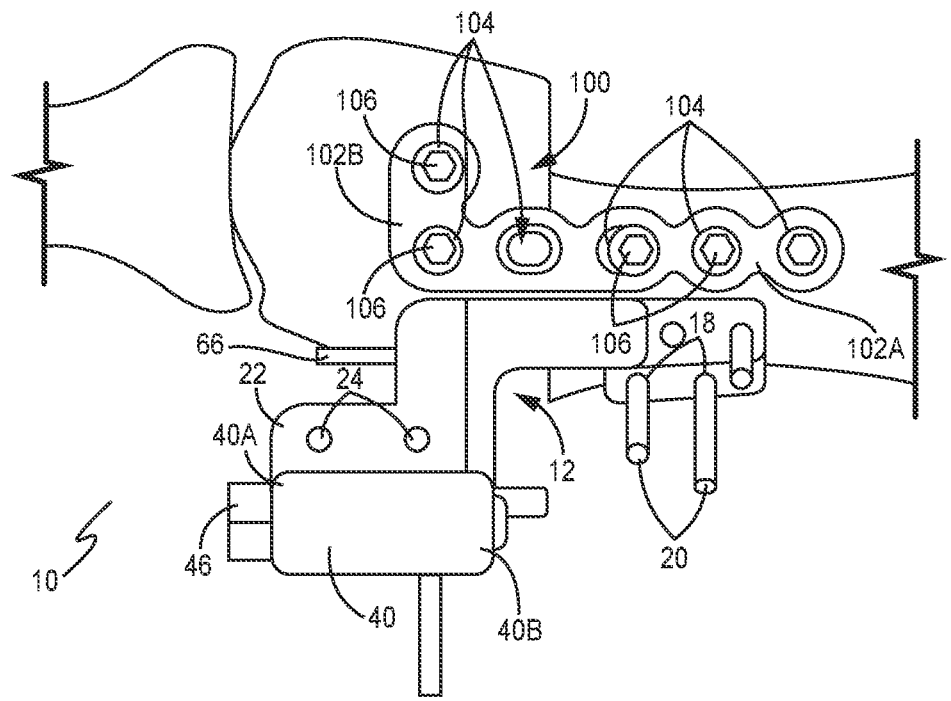
FIG. 2 is a top view of the guide device of FIG. 1A with the slot body removed, according to one embodiment.

As best shown in FIGS. 1A and 2, the jig body 12 has a lip or "seat" 22 as shown at or near a distal end of the body 12 that is configured to receive the slot body 16. The seat 22 has two attachment mechanism openings 24 defined therein (as best shown in FIG. 2), wherein each of the openings 24 is configured to receive an attachment mechanism 26, which in this specific example is an attachment screw 26 as shown in FIGS. 1A-1C. It is understood that any known attachment component or mechanism can be used. Thus, the removable slot body 16, which also has attachment mechanism openings 28 (as best shown in FIG. 10), can be disposed on the seat 22 such that the openings 24, 28 align and the attachment screws 26 can be positioned therethrough to removably attach the slot body 16 to the seat 22 and thus the jig body 12.

Figure 1D:
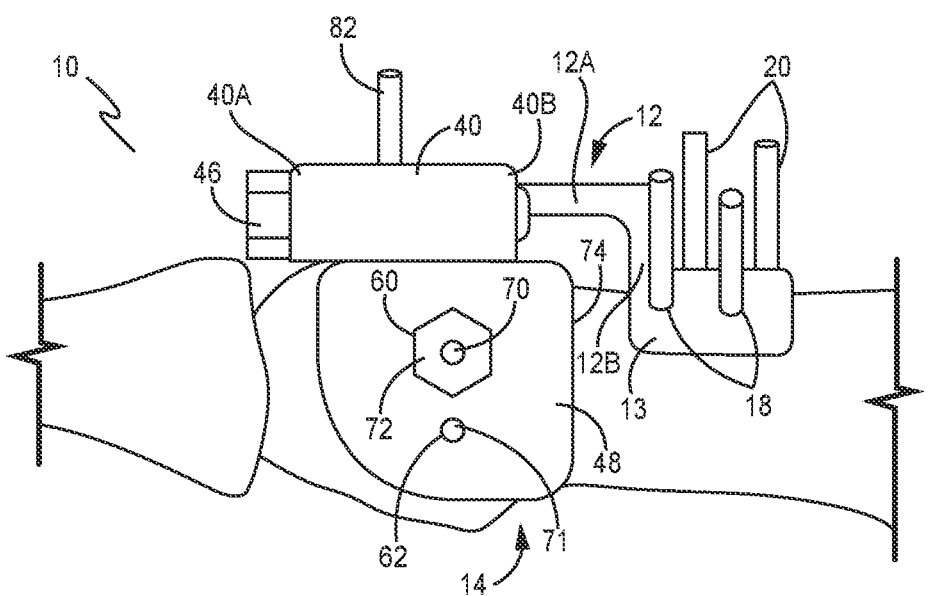
FIG. 1D is a side view of the guide device of FIG. 1A, according to one embodiment.

In one specific implementation, the jig body 12 has two sections 12A, 12B disposed between the bone attachment structure 13 at the proximal end and the guide coupling structure 40 and seat 22 at the distal end, as best shown in FIGS. 1B and 1D. More specifically, the jig body 12 can have a longitudinal section 12A that is substantially parallel to the target bone to which the body 12 is attached and a transverse section 12B that is substantially transverse to the longitudinal axis of the target one. The two sections 12A, 12B can be integrally joined or removably attached together at an elbow 15 as best shown in FIG. 1B and. The transverse section 12B is attached at one end to (or integral with) the bone attachment structure 13, while the longitudinal section 12A is attached at one end to (or integral with) the guide coupling structure 40 and seat 22. Alternatively, the jig body 12 doesn't have two sections with an elbow.

Figure 1E:
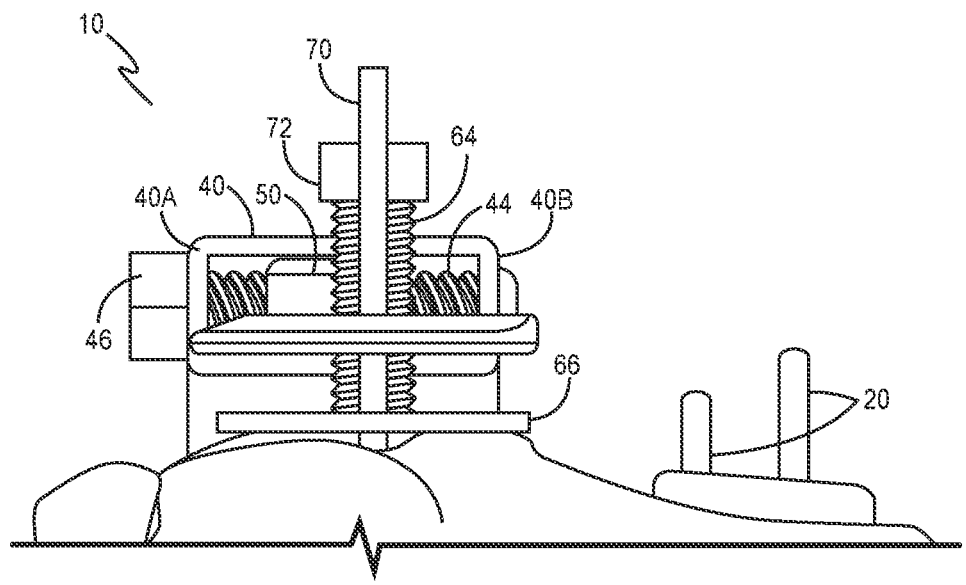
FIG. 1E is a bottom view of the guide device of FIG. 1A, according to one embodiment.
Figure 1F:
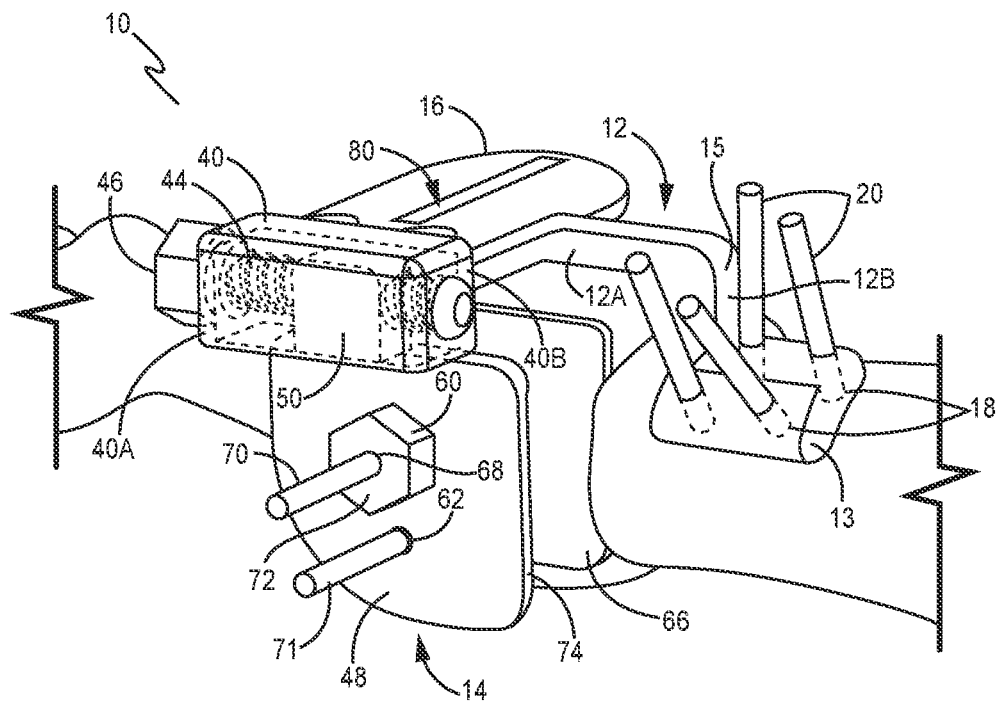
FIG. 1F is another rear perspective view of the guide device of FIG. 1A, according to one embodiment.

In addition, the jig body 12 has a guide coupling structure (also referred to herein as a "frame") 40 having two opposing ends 40A, 40B as best shown in FIGS. 1B and 1D. Each of the ends 40A, 40B has an opening (not shown) defined therein such that the openings receive opposite ends of a threaded, rotatable rod 44 that is threadably coupled to the movable cutting guide 14, as best shown in FIGS. 1E and 1F. The rotatable rod 44 has a head 46 that is configured to couple to a screwdriver (not shown) or other actuation tool such that the screwdriver can rotate the rod 44. The movable guide 14 has a guide body 48 with a projection 50 (also referred to herein as an "attachment body") (as also shown in FIGS. 1E and 1F) extending therefrom with a lumen (not shown) defined therethrough. The lumen (not shown) has a threaded inner surface (not shown) that is mateable with the threads of the rotatable rod 44 such that rotation of the rod 44 causes the projection 50 to be urged longitudinally along the length of the rod 44 as a result of the threaded coupling, thereby causing the movable guide body 48 to be urged along the same path, which is generally parallel to the length of the body 12. As such, the rotatable rod 44 can be actuated (via the screwdriver or other such tool) to move the movable guide 14 as desired along its predetermined path.

The guide body 48 also has two openings 60, 62 defined therein, as best shown in FIG. 1D. The opening 60 is a threaded opening 60 that is sized to receive a threaded transposition mechanism 64, as best shown in FIGS. 1A-B and 1E. The transposition screw mechanism 64 in this specific implementation is a threaded screw 64 with a lumen 68 defined therein (as best shown in FIG. 1B), through which an anchor pin 70 can be disposed as shown. The threaded screw 64 has external threading such that the external threading is mateable with the threading (not shown) on the inner surface (not shown) of the opening 60. Hence, rotation of the threaded screw 64 causes the screw 64 to move laterally/medially as a result of the mated threads of the screw 64 and the opening 60. The screw 64 has a head or mateable feature 72 (as best shown in FIG. 1B) at its proximal end that is configured to couple to a screwdriver (not shown) or other actuation tool such that the screwdriver can rotate the screw 64. The distal end of the screw 64 has a distal plate 66 attached thereto such that the plate 66 can be disposed adjacent to and placed into contact with the target bone, as best shown in FIG. 1A. As such, the screw 64 can be actuated (via the screwdriver or other such tool) to urge the distal plate 66 into contact with the target bone and thereby urge the target bone laterally as desired (thereby "transposing" the bone), as will be described in further detail below. Alternatively, the threaded mechanism 64 can be any mechanism or device for translational coupling to the guide body 48 such that actuation of the mechanism can cause the transposition of the target bone. In addition, as mentioned above, the lumen 68 in the screw 64 is sized to receive an anchor pin 70 such that the anchor pin 70 can be anchored into the target bone.

In addition, the second opening 62 is sized and shaped to receive another anchor pin 71, as best shown in FIG. 1B.

In addition, the guide body 48 of the movable guide 14 has a flat guide edge 74 at its proximal end, as best shown in FIGS. 1B and 1D. As will discussed in further detail below, the flat guide edge 74 is used by the surgeon as the bone saw blade guide, such that the surgeon positions the bone saw blade against the flat guide edge 74 when preparing to cut the target bone, thereby ensuring that the cut is straight, controlled, and uniform.

Figure 3:
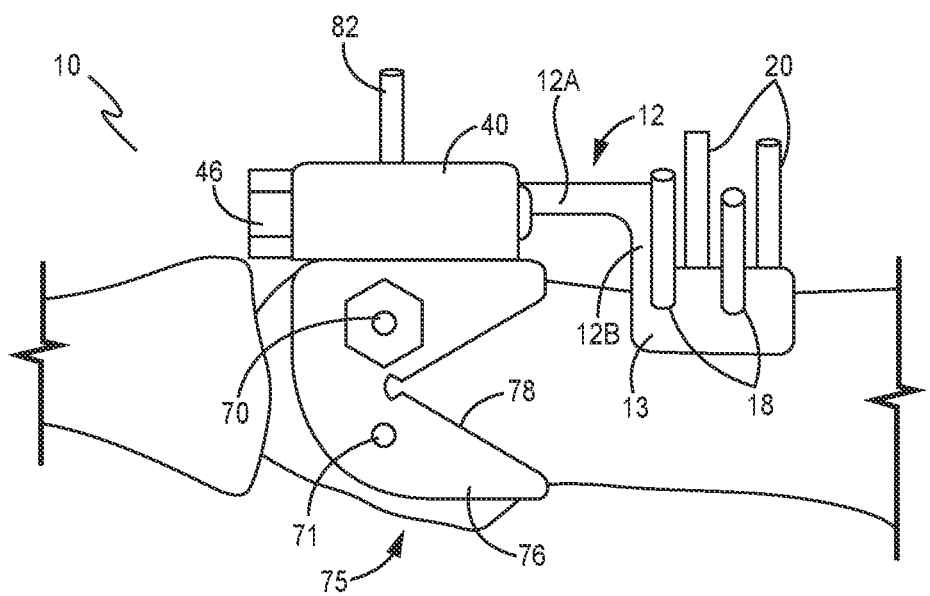
FIG. 3 is another side view of the guide device of FIG. 1A with a V-cut guide body attached thereto, according to one embodiment.

It should be noted at this point that, in certain embodiments, at least two different interchangeable guides can be provided with the various osteotomy procedure system implementations disclosed or contemplated herein. That is, in addition to the flat cut guide 14 as depicted in FIGS. 1A-1D and discussed above, the system also includes a V-cut guide 75, as best shown in FIG. 3, that can be incorporated into the device 10. While the flat cut guide body 48 has a flat guide edge 74 as described above for use to make a straight cut, the V-cut guide body 76 has a V-shaped guide edge 78 (as also shown in FIG. 3). The V-shaped guide edge 78 is used by the surgeon as the bone saw blade guide, such that the surgeon positions the bone saw blade against the V-shaped guide edge 78 when preparing to cut the target bone, thereby ensuring that the cut is controlled and has a uniform V shape, as described in additional detail below.

It is understood that other guide bodies having edges with additional known edge shapes for additional known cutting shapes can also be incorporated into the various system embodiments herein.

The various guide body embodiments disclosed or contemplated herein (including bodies 48, 90) are made of metal or plastic of an appropriate rigidity. More specifically, some exemplary materials that can make up the guide body embodiments include any known medical grade stainless steel alloys, titanium alloys, thermoplastics, and/or thermosets/resins. Alternatively, the bodies can be made of any known material of appropriate rigidity that can be used in such bone treatment devices.

The removable wing 16 has a slot 80 defined therein, wherein the slot 80 extends along a length of the slot body 16. In the specific embodiment herein, the slot 80 is parallel to the longitudinal axis of the slot body 16. In addition, as mentioned above, the slot body 16 also has two attachment screw openings 28 defined therein that are configured to receive two attachment screws 26. The slot 80 is sized to receive an anchor pin, such as pin 82.

The combination of the anchor pin 82 to affix the device 10 at the slot body 16 and the anchor pins 20 to affix the device 10 at the bone attachment structure 13 allows for the fixation of the device 10 at various anatomical locations on various types of bones to ensure stability and alignment. That is, the ability to position the various pins 20, 82 at various angles via the openings 18 of various angles in the attachment structure 13 and the slot 80 in the slot body 16 allows for the pins 20, 82, and thereby the device 10, to be attached to a variety of different anatomical locations.

The various wing embodiments disclosed or contemplated herein (including wing 16) are made of metal or plastic of an appropriate rigidity. Alternatively, the wings can be made of any known material of appropriate rigidity that can be used in such bone treatment devices.

In addition, as best shown in FIG. 2, the system can also include a fixation plate 100. In this specific embodiment, the fixation plate 100 is an L-shaped plate 100 with an elongate section 102A and a transverse distal section 102B. In addition, the plate 100 has various openings 104 defined therein that are configured to receive appropriate bone screws 106 as shown. The transverse distal section 102B is intended to extend laterally along the path of the transposition of the bone that occurs during the bone adjustment procedure, as will be described in further detail below. Thus, the transverse distal section 102B facilitates attachment to and fixation of the target bone. As will also be described in further detail below, the fixation plate 100 is not utilized within the system until the removable wing 16 has been removed from the jig body 12 of the device 10.

The various fixation plate embodiments disclosed or contemplated herein (including plate 100) are made of an appropriate metal, such as titanium or stainless steel. Alternatively, the plates can be made of any known metal having the appropriate characteristics. In addition, any of the attachment mechanisms and/or screws are made of similar metals.

Another embodiment of a guide device or "jig" 210 is depicted in FIGS. 4A-5E, according to a further implementation. The jig 210 has an device body 212, a movable cutting guide 214 movably coupled to the body 212 at a guide coupling structure 240, and a removable slot body (also referred to herein as a "wing") 216 removably attached to the jig body 212. Each of these components and the additional features and components therein are substantially similar to and have substantially the same functions and characteristics as the corresponding components and features in the jig 10 embodiment described above and depicted in FIGS. 1A-3, except as described in further detail below.

Figure 4A:
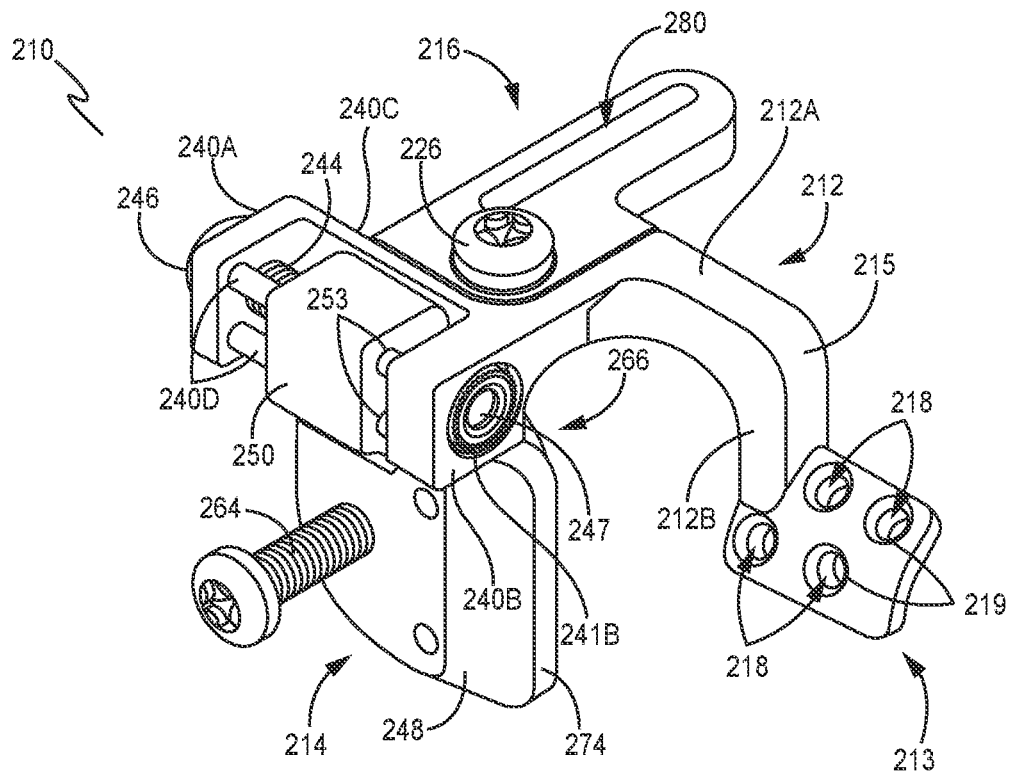
FIG. 4A is a perspective rear view of a guide device with a flat cut guide attached thereto, according to another embodiment.
Figure 4B:
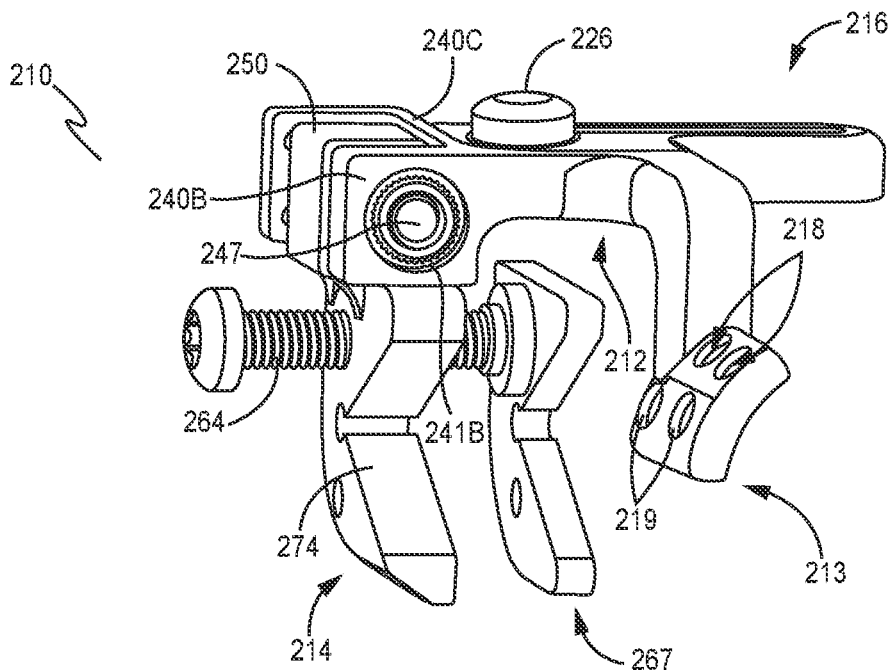
FIG. 4B is another perspective rear view of the guide device of FIG. 4A with a V-cut guide attached thereto, according to one embodiment.
Figure 5A:
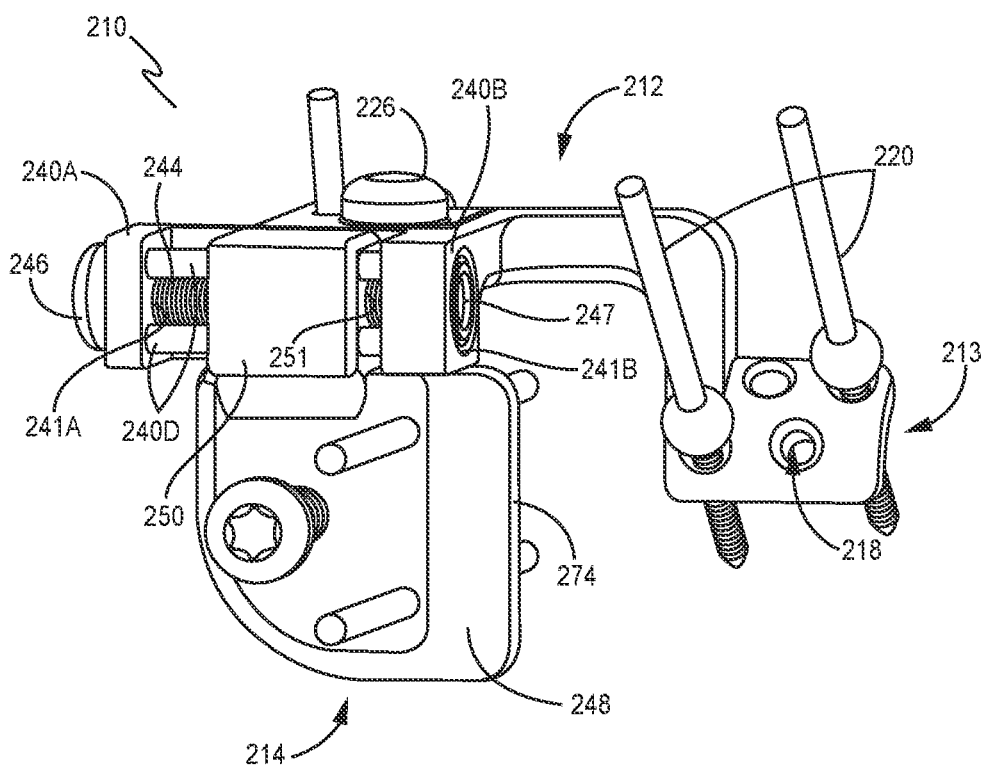
FIG. 5A is another perspective side view of the guide device of FIG. 4A with a flat cut guide attached thereto, according to one embodiment.
Figure 5B:
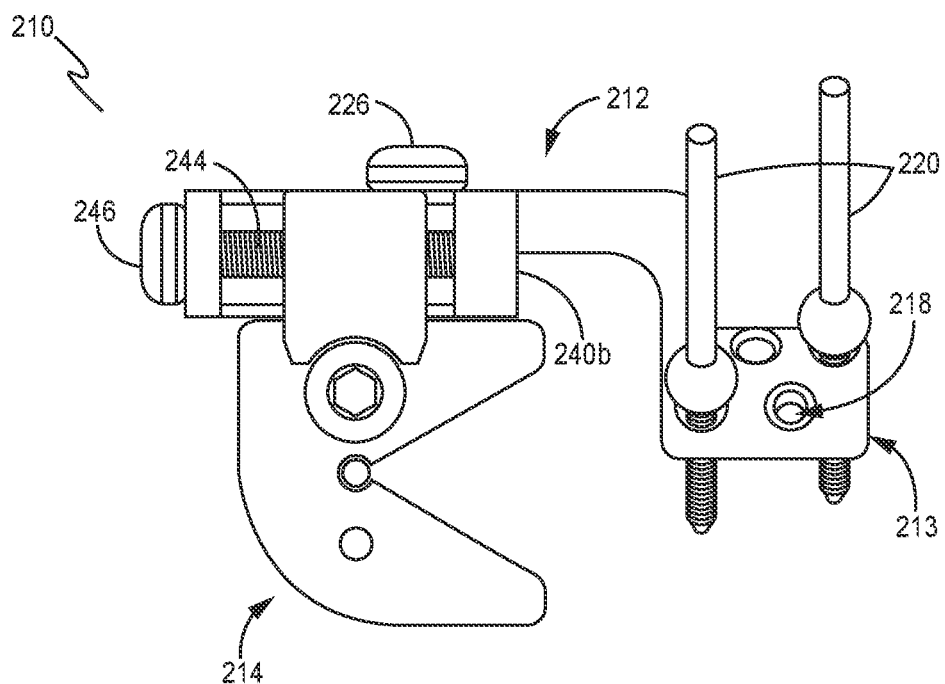
FIG. 5B is a side view of the guide device of FIG. 4A with a V-cut guide attached thereto, according to one embodiment.
Figure 5C:
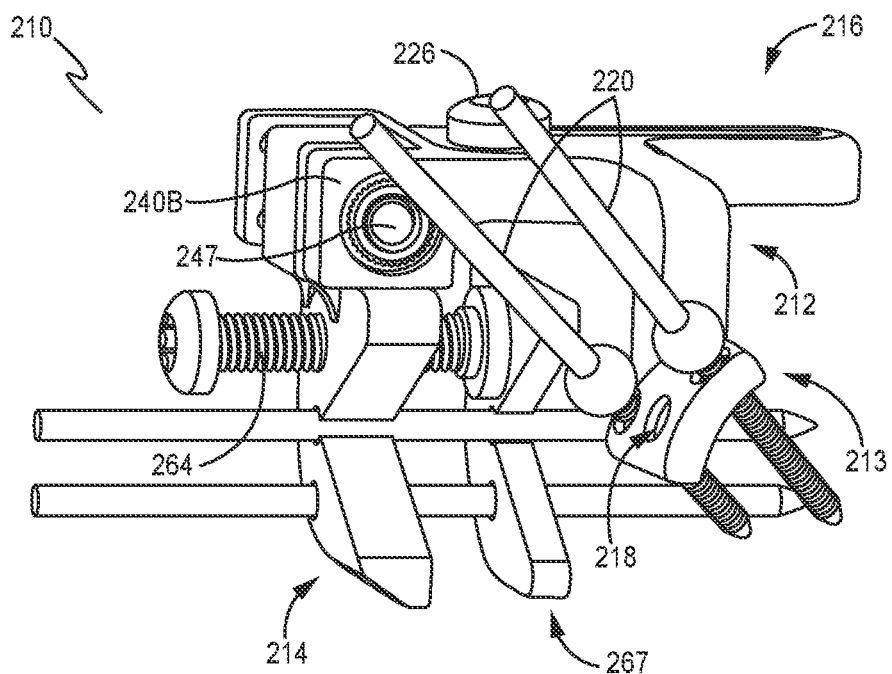
FIG. 5C is another perspective view of the guide device of FIG. 4A with a V-cut guide attached thereto, according to one embodiment.

In this embodiment, the jig body 212 has a bone attachment structure (also referred to as a "dorsal fixation section") 213 at or near a proximal end of the body 212, along with the guide coupling structure 240 discussed above at or near the distal end. As best shown in FIGS. 4A and 4B, the bone attachment structure 213 has four anchor openings 218 defined therein, wherein each of the anchor openings 18 is configured to receive an anchor pin 220 as shown such that the anchor pins 220 are embedded into or "anchored" in the dorsal portion of the target bone. In this specific implementation, as best shown in FIGS. 5A-5C, the anchor pins 220 are standard K wires or olive wires 220 and the anchor openings 218 have rounded edges 219 as shown that are shaped to mate with the olive 221 of the olive wires 220 such that the anchor pins 220 are more firmly seated within the openings 218. More specifically, the round shape of the olive 221 of the olive wires 220 can be disposed further into the openings 218 and with a more secure fit as a result of the rounded edges 219. Alternatively, the openings 218 can be shaped in any known fashion or have any known features that can provide for a more stable mating with the k wires 220 than afforded by an opening without such shaping or feature. Alternatively, the anchor pins (including 220) described herein can be any known elongate anchoring or fixation mechanisms or devices that can be used with bone fixation devices and can mate with the openings 218 herein.

Figure 4C:
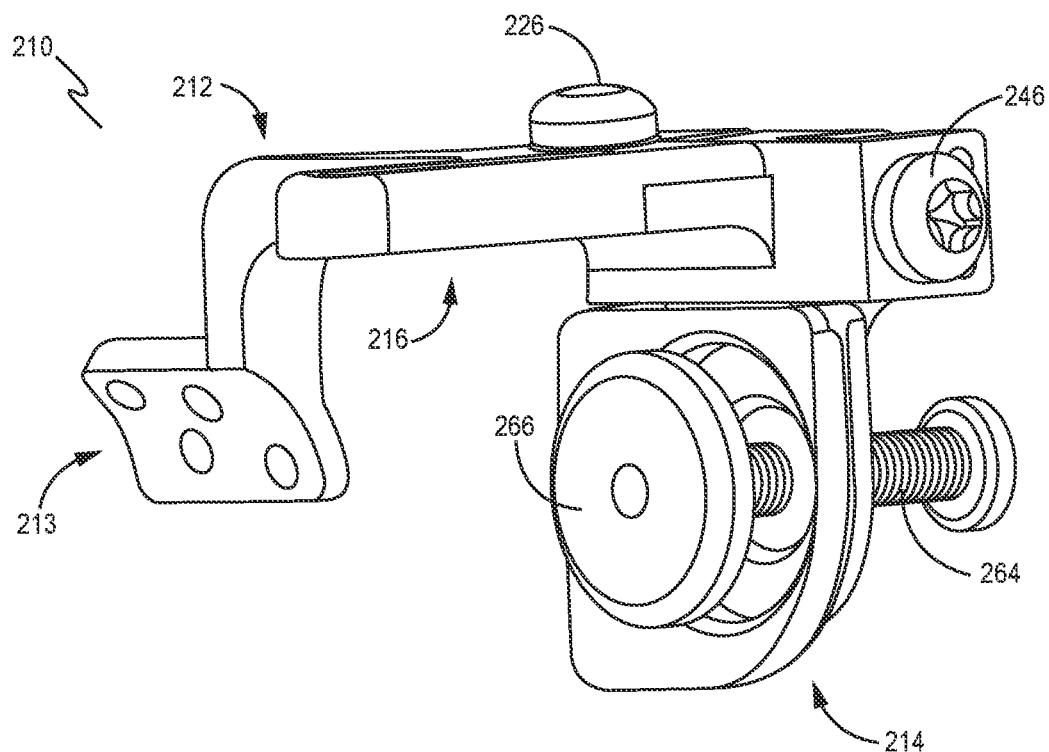
FIG. 4C is a perspective side view of the guide device of FIG. 4A with a flat cut guide attached thereto, according to one embodiment.
Figure 5D:
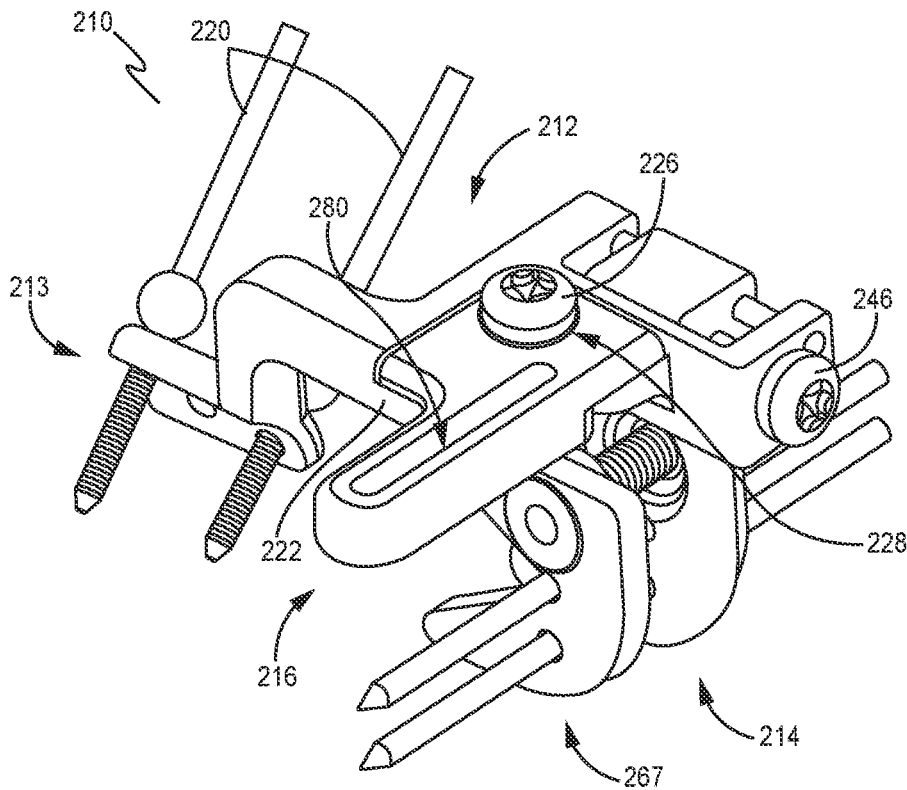
FIG. 5D is a perspective side view of the guide device of FIG. 4A with a V-cut guide attached thereto, according to one embodiment.
Figure 5E:
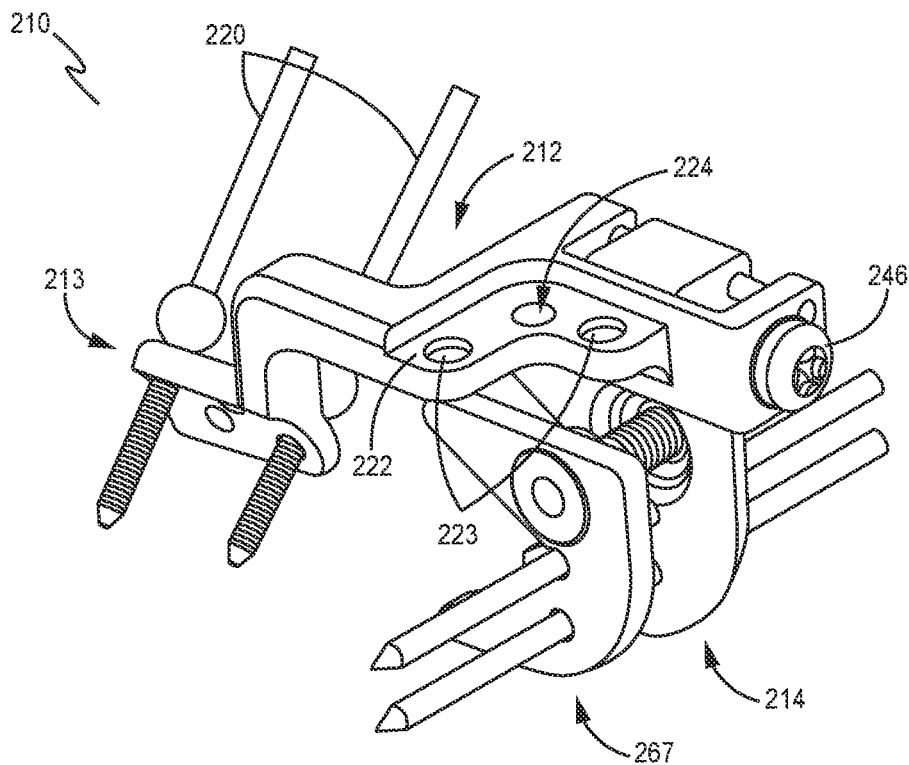
FIG. 5E is another perspective side view of the guide device of FIG. 5D with the slot body removed, according to one embodiment.

As best shown in FIGS. 5D and 5E, the jig body 212 has a seat 222 at or near a distal end of the body 212 as shown that is configured to receive the slot body 216. In this implementation, as best shown in FIG. 5E, the seat 222 has one attachment mechanism opening 224 defined therein (instead of two), wherein the opening 224 is configured to receive an attachment mechanism 226, which in this specific example is an attachment screw 226 as shown in FIGS. 4A-5D. In this specific embodiment, the attachment screw 226 has a head that receives a known T-10 driver, and the head 246 on the device 210 is the same, thereby simplifying use of the device 210 by eliminating the need for more than one driver for operating the device 210. Alternatively, the various heads on the device 210 can share any other known configuration that allows for the use of any other known single tool. Thus, the removable slot body 216, which also has an attachment mechanism opening 228 (as best shown in FIG. 5D), can be disposed on the seat 222 such that the opening 224, 228 align and the attachment screw 226 can be positioned therethrough to removably attach the slot body 216 to the seat 222 and thus the jig body 212. Alternatively, it is understood that any known attachment component or mechanism can be used. In addition, according to this specific embodiment, the seat 222 also has two indentations or recesses 223 defined therein that are configured to receive pins or protrusions (not shown) extending from the underside of the slot body 216. The indentations 223 mate with the protrusions such that they assist with fixedly securing the body 216 to the seat 222 and thus help to maintain the alignment of the body 216 thereon.

In this specific implementation, the guide coupling structure (also referred to herein as a "frame") 240 has two opposing ends 240A, 240B that are coupled together with a wall 240C on one side and with two rods 240D on the other as best shown in FIG. 4A. Each of the ends 240A, 240B has openings 241A, 241B defined therein (as best shown in FIG. 5A) such that the openings 241A, 241B receive opposite ends of a threaded, rotatable rod 244 that is threadably coupled to the movable cutting guide 214, as best shown in FIGS. 4A and 5A. In this embodiment, the projection 250 of the moveable cutting guide 214 has three lumens 251, 253 defined therethrough. More specifically, the projection 250 has a larger first lumen 251 (as best shown in FIG. 5A) with a threaded inner surface (not shown) that is mateable with the threads of the rotatable rod 244 such that the rod 244 can be disposed through the first lumen 251 and rotation of the rod 244 causes the projection 250 to be urged longitudinally along the length of the rod 244 as a result of the threaded coupling, thereby causing the movable guide body 248 to be urged along the same path, which is generally parallel to the length of the body 212. In addition, the projection 250 has two smaller second lumens 253 (as best shown in FIG. 4A) that are configured to receive the two rods 240D such that the projection 250 can slide along the rods 240D as the projection 250 is moved by the rotatable rod 244.

In addition, according to certain implementations, the guide coupling structure 240 can have a recessed rod end 247 disposed within the opening 241B of structure end 240B as best shown in FIGS. 4A, 4B, 5A, 5C. The rod end 247 is one end of the threaded, rotatable rod 244 that is threadably coupled to the movable guide 214 as discussed above. The rod end 247 in this embodiment is recessed such that it does not protrude out from the body end 240B. As such, the rod end 247 is flush with or recessed into the end 240B such that it will not block or be contacted by any cutting device (as described elsewhere herein) that is positioned against the cutting guide edge 274. As such, the recessed rod end 247 allows for ease of use when positioning the cutting device against the edge 274.

In accordance with certain embodiments herein, as best shown in FIG. 4C, the distal (or "push") plate 266 coupled to the transposition screw mechanism 264 and disposed adjacent to and placed into contact with the target bone has a substantially circular shaped face. As such, when the screw 264 is rotated (via a screwdriver or other such tool) to urge the distal plate 266 into contact with the target bone as discussed elsewhere herein, the circular-shaped face can be allowed to rotate along with the screw 264 and urge the bone laterally. The circular shape allows for the rotation of the plate 266 itself, rather than requiring the plate to move laterally without rotation. Alternatively, the V-cut push plate 267 as shown in FIGS. 4B and 5C-5E can still be a non-circular, non-rotating plate 267 that replicates the general shape of the guide 214.

The removable wing 216 in the embodiment of FIGS. 4A-5E is a narrower wing 216 in comparison to the wing 16 discussed above. That is, the wing 216 is a smaller structure having a smaller distance between the outer edge of the wing 216 and the slot 280 defined therein. In one embodiment, the slot 280 has a length ranging from about 12 mm to about 20 mm and a width ranging from about 1 mm to about 3 mm. Alternatively, the slot 280 has a length ranging from about 14 mm to about 18 mm and a width ranging from about 1.5 mm to about 2.5 mm. In a further alternative, the slot 280 has a length of about 16 mm and a width of about 1.8 mm to about 2.2 mm. Further, the projection portion of the slot body 216 extending from the device 210 can have a width ranging from about 4 mm to about 8 mm. Alternatively, the projection portion can have a width ranging from about 5 mm to about 7 mm. In a further alternative, the projection portion has a width of about 5.8 mm to about 6.2 mm.

In use, the various osteotomy procedure systems disclosed or contemplated herein can be utilized in the following general fashion to allow a surgeon to perform a consistently accurate osteotomy procedure to treat a bone deformity, such as, for example, hallux valgus. That is, the system implementations include a jig (such as jig 10 or jig 210) with a guide (such as guides 14, 75, or 214) having a predetermined edge shape that is used to assist the surgeon in making a consistently accurate osteotomy configuration and further allows mechanical transposition of the bone head in the lateral direction using the transposition screw mechanism (such as either of mechanisms 64 or 264) without the complications of manual manipulation and the resulting lack of uniformity and wasted time. The jig (such as jig 10 or jig 210) then retains the reduced osteotomy in the desired alignment while the surgeon performs a scan or X-ray to determine the effectiveness of the deformity correction and, once the effectiveness is confirmed or adjustments are made, the fixation plate 100 is attached to the bone to fixate the two pieces in the desired position.

Focusing now on the details of the method of using the system (according to one embodiment), the first step, in some cases, is to use a bone saw (not shown) to flatten the dorsal aspect of the first metatarsal head and round off the dorsal medial corner. Alternatively, this step can be taken with the equivalent portions of any target bone. This optional step can aid in both jig (such as jig 10 or 210) and fixation plate (such as plate 100) application and can also assist with optionally rotating the head when correcting frontal plane alignment, as will be described in further detail below.

The next step (or first step if the shaping step is skipped) is to select an appropriate jig (such as jig 10 or 210), and/or an appropriate guide, depending on whether the surgeon wants to use a straight cut or a V-shaped cut. While the specific components of the jig 10 are discussed specifically for the remainder of this discussion, it is understood that the same steps can be taken with the corresponding components of the jig 210. Once the jig 10 is selected, the wing body 16 of that jig 10 is then attached to the target bone (such as a metatarsal) with the anchoring pin 82. The pin 82 is inserted into the bone (into the dorsal side and toward the plantar side) through and along the medial edge of the slot 80 in the wing body 16. In certain embodiments in which the flat cut guide 14 is selected to make a straight cut, the anchoring pin 82 is inserted at an oblique angle such that the pin 82 can be used to assist with frontal plane rotation. That is, at the appropriate time, the surgeon can grasp the pin 82 and urge it along the slot opening 80, thereby rotating the bone around it's longitudinal axis as described in additional detail below. Once the wing body 16 is attached via the anchoring pin 82, the jig body 12 is then attached to the dorsal medial aspect of the mid-bone (such as mid-metatarsal) shaft via insertion of anchoring pins 20 through the proximal anchoring openings 18.

Once the jig body 12 and wing 16 are attached to the bone, the surgeon can make the desired cut by positioning the saw blade along the guide edge and making the cut from the medial to the lateral side of the bone. If the surgeon selected the flat cut guide 14, then the surgeon places the blade against the flat edge 74 and makes the straight cut. Alternatively, if the surgeon selected the V-cut guide 75, then the surgeon places the blade against the V-shaped edge 78 and makes the V-shaped cut. In either case, the jig 10 allows for a consistent osteotomy configuration, location, and cut at the neck of the bone to minimize variability, random cuts, and surgeon struggle.

If the flat cut option was selected, the next step involves the surgeon rotating the bone (such as metatarsal) head around its longitudinal axis to correct frontal plane deformity by urging the anchoring pin 82 to a substantially vertical position from its initial angled position as described above such that the anchoring pin 82 is disposed at a substantially 90 degree angle in relation to the plane of the wing.

After rotation in the flat cut option, or once the V-shaped cut has been made in the V-shaped cut option, the transposition anchoring pin 70 is then inserted from the medial side toward the lateral side through the lumen 68 of the transposition screw 64. Once the pin 70 is inserted into the target bone, the cut bone is distracted (urged distally) from the base bone from which it was cut. More specifically, the screwdriver is coupled to the head 46 of the compression rod 44 and rotated to cause the rod 44 to rotate, thereby urging the guide body 14 (or 75) distally, which urges the transposition anchoring pin 70 (and thus the bone) distally until there is a desired gap between the target (cut) bone and the proximal bone.

Once the target portion of the bone has been distracted, the screw driver (not shown) is then used to turn the transposition screw 64 by mating the screwdriver with the head 68 of the screw 64 and then rotating the screwdriver. In one embodiment, the screwdriver is urged clockwise, thereby causing the transposition screw 64 to be urged in the lateral direction, thereby resulting in the distal plate 66 contacting and pushing the bone head in the lateral direction. Once the desired amount of transposition has occurred (that is, the desired intermetatarsal angle (IMA) correction is achieved when the target bone is a metatarsal), such as the transposition depicted in FIG. 10, the osteotomy gap is closed. That is, the screwdriver is coupled to the head 46 of the compression rod 44 and rotated to cause the rod 44 to rotate, thereby urging the guide body 14 (or 75) proximally, which urges the transposition anchoring pin 70 (and thus the bone) proximally until it is in contact with the proximal bone, thereby closing any gap existing between the two bones. At this point, the surgeon can image the construct to check anatomic correction and adjustments can be made prior to dorsal plate fixation.

Once the bones are positioned as desired, the wing body 16 is removed. That is, the screwdriver is used to remove the attachment screws 26 and then the wing body 16. This provides an open space on the dorsal portion of the bone. At this point, the fixation plate 100 can be positioned dorsally with the transverse section 102B centered on the head of the bone (such as the metatarsal). Once positioned as desired, the fixation plate 100 is attached to the bones via screws 106 that are inserted through the openings 104 and into the bone. According to one embodiment, the screws 106 are inserted in a particular order. For example, in one embodiment, a first screw 106 is inserted through the opening 104 at the intersection of the elongate section 102A and the transverse section 102B, and then a second screw 106 is inserted through one of the openings 104 in the elongate section 102A. At this point, the anchoring pins 20 are removed from the proximal anchoring openings 18 prior to tightening for compression. The remaining screws 106 are placed through the plate 100 from the dorsal side toward the plantar side. Alternatively, the screws 106 can be inserted in any order.

The remaining anchoring pins are then removed and the entire jig 10 is removed. If necessary, the surgeon can now use a bone saw to remodel the medial bump. Finally, the wound is closed.

As mentioned above, unlike known fixation plates and procedures, the fixation plate 100 is positioned on the dorsal side of the bone (rather than the medial side) to avoid medial shoe pressure. Further, the transverse section 102B of the fixation plate 100 (and the resulting L shape) allows for the plate 100 to match the L shape of the bone following lateral transposition of the head fragment. This L-shaped plate allows multiple transverse screws to be inserted therethrough, which results in the screws to be inserted into dorsal cortical bone in the distal fragment, which is not possible with other forms of screw fixation. Once in place, the fixation plate 100 prevents dorsal displacement, plantar displacement and especially prevents the head from tipping into the interspace despite maximum lateral transposition. The surgeon can therefore push the limits of correction to routinely shift the head laterally to the point of 50% overlap and still allow immediate weight bearing. The locking nature of the plate/screw interface and thin plate design can minimize dorsal irritation and the subsequent need for future hardware removal.

Although the various embodiments have been described with reference to preferred embodiments, persons skilled in the art will recognize that changes may be made in form and detail without departing from the spirit and scope thereof.

What is claimed is:
1. A method of performing an osteotomy, the method comprising:
    positioning an osteotomy device adjacent to a target bone, the osteotomy device comprising:
        (a) a device body comprising:
            (i) a bone attachment structure; and

(ii) a guide coupling structure comprising a rod rotatably associated with the coupling structure;

(b) a movable cutting guide threadably coupled to the rod; and (c) a slot body removably attachable to the device body, wherein the slot body comprises a transverse slot defined within the slot body;

inserting a first anchoring pin through the transverse slot and into the target bone;

inserting a second anchoring pin through an opening defined in the bone attachment structure and into the target bone;

making a desired cut in the target bone with a saw blade positioned against the movable cutting guide, resulting in a base bone and a cut bone;

inserting a transposition mechanism through the movable cutting guide and into the cut bone;

urging the cut bone distally from the base bone by rotating the rod associated with the coupling structure;

urging the cut bone laterally by actuating the transposition mechanism;

urging the cut bone proximally into contact with the base bone by rotating the rod associated with the coupling structure;

removing the slot body from the device body; and attaching a fixation plate to the cut bone and the base bone.

2. The method of claim 1, wherein the movable cutting guide comprises a transposition mechanism threadably coupled thereto, wherein the transposition mechanism comprises a rotatable elongate body and a distal plate attached to a distal end of the rotatable elongate body.

3. The method of claim 2, wherein the distal plate is a rotatable circular plate.

4. The method of claim 2, wherein the rotatable elongate body is a threaded rotatable elongate body disposed through a threaded guide lumen defined in the movable cutting guide.

5. The method of claim 1, wherein the movable cutting guide comprises a proximal guide edge.

6. The method of claim 1, wherein the moveable cutting guide comprises an attachment body, wherein the attachment body comprises a threaded attachment lumen.

7. The method of claim 6, wherein the rod comprises a threaded rod disposed within and threadably coupled with the threaded attachment lumen.

8. The method of claim 1, wherein the movable cutting guide comprises:

(a) a first opening defined in the movable cutting guide, the first opening comprising a threaded opening configured to receive a transposition mechanism threadably coupled therein, wherein the transposition mechanism comprises a threaded rotatable elongate body and a distal plate attached to a distal end of the rotatable elongate body; and (b) a second opening defined in the movable cutting guide, the second opening configured to receive an attachment pin.

9. The method of claim 1, wherein the bone attachment structure comprises at least two fixation screw openings defined therein, wherein the bone attachment structure has a curved face configured to be contactable with the target bone.

10. The method of claim 1, wherein the moveable cutting guide is moveable along a path substantially parallel with a length of the target bone.

11. The method of claim 1, wherein the moveable cutting guide comprises a transposition rod threadably coupled to the moveable guide, wherein the transposition rod comprises a distal plate attached to a distal end of the transposition rod, wherein rotation of the transposition rod causes transverse movement of the transposition rod in relation to a longitudinal axis of the target bone.

* * * * *